United States Patent
Zukowski

(10) Patent No.: US 10,010,392 B1
(45) Date of Patent: Jul. 3, 2018

(54) INDWELLING VALVE ACTUATED URINARY CATHETER

(71) Applicant: Stanislaw L Zukowski, Flagstaff, AZ (US)

(72) Inventor: Stanislaw L Zukowski, Flagstaff, AZ (US)

( * ) Notice: Subject to any disclaimer, the term of this patent is extended or adjusted under 35 U.S.C. 154(b) by 0 days.

(21) Appl. No.: 15/696,364

(22) Filed: Sep. 6, 2017

(51) Int. Cl.
| | |
|---|---|
| *A61F 2/00* | (2006.01) |
| *A61F 2/02* | (2006.01) |
| *A61M 27/00* | (2006.01) |
| *A61M 25/06* | (2006.01) |
| *A61M 39/22* | (2006.01) |

(52) U.S. Cl.
CPC ....... *A61F 2/0009* (2013.01); *A61M 25/0662* (2013.01); *A61M 39/22* (2013.01)

(58) Field of Classification Search
CPC . A61F 2/0009; A61M 25/0662; A61M 39/22; A61M 25/0017; A61M 25/04; A61M 2025/0004
USPC ...................................... 600/29–32; 604/544
See application file for complete search history.

(56) References Cited

U.S. PATENT DOCUMENTS

| | | | |
|---|---|---|---|
| 4,432,757 A | 2/1984 | Davis, Jr. | |
| 4,932,938 A | 6/1990 | Goldberg et al. | |
| 4,946,449 A * | 8/1990 | Davis, Jr. | .......... A61M 25/0075 |
| | | | 128/DIG. 25 |
| 5,041,092 A | 8/1991 | Barwick | |
| 5,112,306 A * | 5/1992 | Burton | .................. A61F 2/0027 |
| | | | 128/DIG. 25 |
| 5,707,357 A | 1/1998 | Mikhail et al. | |
| 6,050,934 A * | 4/2000 | Mikhail | ................ A61F 2/0009 |
| | | | 128/DIG. 25 |
| 6,162,201 A * | 12/2000 | Cohen | ............... A61M 25/0075 |
| | | | 604/101.01 |
| 6,234,956 B1 * | 5/2001 | He | ........................ A61F 2/0018 |
| | | | 600/30 |
| 8,096,986 B2 | 1/2012 | Armistead | |
| 8,475,435 B2 | 7/2013 | Magnus Bolmsjo et al. | |
| 8,633,268 B2 | 1/2014 | Lawson et al. | |
| 9,173,753 B1 * | 11/2015 | Zukowski | ................. A61F 2/90 |
| 2003/0208183 A1 * | 11/2003 | Whalen | ................. A61F 2/0027 |
| | | | 604/544 |
| 2005/0059929 A1 * | 3/2005 | Bolmsjo | ........... A61M 25/0017 |
| | | | 604/96.01 |
| 2005/0101924 A1 * | 5/2005 | Elson | ..................... A61F 5/453 |
| | | | 604/349 |

(Continued)

*Primary Examiner* — Navin Natnithithadha
*Assistant Examiner* — Sunita Reddy
(74) *Attorney, Agent, or Firm* — Invention To Patent Services; Alex Hobson

(57) ABSTRACT

An indwelling valve actuated urinary catheter has an inner catheter having an inlet port configured on a distal end and for locating within the bladder and a sheath that slides over the inner catheter to produce a valve. The sheath extends over the inlet port when the valve is in a closed position and manipulation of a valve actuator on the proximal end, located within the penis, opens the valve. The sheath may include a window that is aligned with the inlet port when the sheath is moved to open the valve. The valve actuator may comprise a proximal nodule and a distal nodule that are configured within the urethra along the penis. Manual manipulation of the valve actuator through the penis, such as by pinching the penis, moves the proximal and distal nodules with respect to each other to open or close the valve.

16 Claims, 9 Drawing Sheets

(56) References Cited

U.S. PATENT DOCUMENTS

| | | | |
|---|---|---|---|
| 2005/0101941 A1* | 5/2005 | Hakky | A61M 25/0017 604/544 |
| 2006/0167438 A1 | 7/2006 | Kalser et al. | |
| 2006/0205997 A1 | 9/2006 | Whalen | |
| 2006/0287570 A1 | 12/2006 | Whalen | |
| 2007/0078389 A1 | 4/2007 | Whalen | |
| 2008/0114286 A1 | 5/2008 | Hamel et al. | |
| 2010/0312225 A1* | 12/2010 | Armistead | A61M 25/0017 604/544 |
| 2012/0004645 A1 | 1/2012 | Dastani | |
| 2013/0173016 A1* | 7/2013 | Devereux | A61F 2/88 623/23.66 |
| 2013/0197486 A1* | 8/2013 | Aaronson | A61M 25/0017 604/544 |
| 2015/0196730 A1* | 7/2015 | O'Callaghan | A61M 25/0017 604/544 |

\* cited by examiner

INDWELLING VALVE ACTUATED URINARY CATHETER

BACKGROUND OF THE INVENTION

Field of the Invention

The invention is directed to indwelling catheters having a valve on the distal end of the catheter that extends into the bladder that is manipulated by a valve actuator located within the penis.

BACKGROUND

Catheters are routinely inserted through the urethra and extend into the bladder to expel urine. Indwelling catheters typically have a portion that extends out of the penis that can be manipulated to allow urine to be expelled. In some cases, a valve is configured on the outer extended portion of the catheter. Manipulation of the outer extended portion is cumbersome and prevents a person from participating in intercourse. Some indwelling catheters are configured within the urethra and do not extend out from the penis but require insertion of an instrument to initiate the flow of urine. This is cumbersome and embarrassing for the user as they have to carry instruments with them to restroom. These indwelling catheters also retain urine as the valve is configured on the proximal end, or end closest to the tip of the penis and the full catheter is prone to leaking as it is full of urine at all times.

SUMMARY OF THE INVENTION

The invention is directed to an indwelling valve actuated urinary catheter that comprises an inner catheter having an inlet port configured on a distal end and for locating within the bladder and a sheath that slides over the inner catheter to produce a valve. The sheath may extend over the inlet port when the valve is in a closed position and may be manipulated by a valve actuator on the proximal end, and located within the penis, to move and open the valve. The sheath may be moved toward the valve actuator and the distal end of the sheath may be moved to open the valve. The sheath may comprise a window and the sheath may be moved to align the window with the inlet port to open the valve. The inner catheter may me moved within the sheath, or moved with respect to the sheath, and to align a window in the sheath with the inlet port. The valve actuator may comprise a proximal nodule and a distal nodule that are configured within the urethra along the penis. Manual manipulation of the valve actuator through the penis, such as by pinching the penis, moves the proximal and distal nodules with respect to each other to open or close the valve.

An exemplary indwelling valve actuated urinary catheter allows a user to open and close the valve by simple manual manipulation of the valve actuator within the penis. The exemplary indwelling valve actuated urinary catheter will remain empty of urine as the valve is located within the bladder and not on the proximal end as is the case with most urinary catheters. In addition, an exemplary indwelling valve actuated urinary catheter may comprise a retaining feature that keeps the valve open so that the user can expel urine from their bladder without holding the valve open.

An exemplary valve actuator comprises a proximal and distal nodule that are moved with respect to each other to change an offset distance between them to open and close the valve. The sheath may be attached to the distal nodule and movement of the sheath by movement of the distal nodule to or away from the proximal nodule may open the valve from a closed position. The inner catheter may be attached to the proximal nodule and movement of the inner catheter by movement of the proximal nodule to or away from the distal nodule may open the valve from a closed position. A spring element may be configured between the proximal and distal nodules and may provide an extension force to keep an expanded offset distance to keep the valve closed or may provide a retraction force to maintain a retracted offset distance to keep the valve closed. A user may have to overcome the force of the spring element to move the proximal and distal nodule with respect to each other to open the valve.

An exemplary indwelling valve actuated urinary catheter may comprise a retaining feature that keeps the valve open to allow a user to continue to expel urine or urinate without holding the nodules at a required offset distance. An exemplary retaining feature comprise a protrusion and/or detent in the inner surface of the sheath and outer surface of the inner catheter, or the interface, that creates an interference to maintain an offset distance. For example, a sheath may comprise toroid shaped or ring-shaped protrusion along the inner surface that seats into a ring-shaped detent around the outer surface of the inner catheter. In another embodiment, the sheath comprises a ring-shaped protrusion on the inside surface and the inner catheter comprises a ring shaped protrusion from the outer surface and these two protrusion are force past each other when the proximal and distal nodules are moved to open the valve to create an interference that keeps the valve open. The interference force of the retainer feature, or force required to move the sheath and inner conduit with respect to each other to dislodge the retainer feature may be greater than the spring element force.

An exemplary indwelling valve actuated urinary catheter may also comprise one or more prostate apertures to allow the prostate to expel secretions through the catheter. A sheath prostate aperture may be aligned with an inner prostate aperture, or prostate aperture in the inner catheter while the valve is in a closed position and/or when in an open position. In an exemplary embodiment, a plurality of prostate apertures may be partially aligned while in the closed and/or open position.

An exemplary indwelling valve actuated urinary catheter comprises a window in the sheath that is aligned with the inlet port by moving the sheath, or distal nodule with respect to the proximal nodule to open the valve. The window may be configured more proximal to the valve actuator than the inlet port requiring the offset distance between the proximal and distal nodules to be increased to align the window with the inlet port. In this embodiment, the spring element would provide an retraction force to keep the window in the sheath proximal to the inlet port and the valve closed when not in use. The window may be configured more distal to the valve actuator than the inlet port requiring the offset distance between the proximal and distal nodules to be decreased to align the window with the inlet port. In this embodiment, the spring element would provide an extension force to keep the window in the sheath distal the inlet port and the valve closed when not in use.

An exemplary indwelling valve actuated urinary catheter comprises a sheath having a distal end that is more distal than the inlet port when in closed position. The distal nodule may be moved closer to the proximal nodule to move the distal end of the sheath over the inlet port to open the valve. In this embodiment, the spring element would provide an extension force to keep the distal end of the sheath distal the inlet port and the valve closed when not in use.

An exemplary indwelling valve actuated urinary catheter comprises a window in the sheath that is aligned with the inlet port by moving the inner catheter, or proximal nodule with respect to the distal nodule to open the valve. The window may be configured more distal to the valve actuator than the inlet port requiring the offset distance between the proximal and distal nodules to be decreased to align the window with the inlet port. In this embodiment, the spring element would provide an extension force to keep the window in the sheath distal the inlet port and the valve closed when not in use. The window may be configured more distal to the valve actuator than the inlet port requiring the offset distance between the proximal and distal nodules to be increased to align the window with the inlet port. In this embodiment, the spring element would provide a retraction force to keep the window in the sheath distal to the inlet port and the valve closed when not in use.

An exemplary indwelling valve actuated urinary catheter may be provide in a size to fit a person's anatomy. The length may be 10 cm or more, 20 cm or more, 30 cm or more, 40 cm or more, and any range between and including the length values provided. The diameter of an exemplary indwelling valve actuated urinary catheter may be 10 French (Fr) or more, 20Fr or more, about 40Fr or more, about 50Fr or less and any range between and including the French sizes provided.

A method of urinating utilizing an exemplary indwelling valve actuated urinary catheter comprises the steps of inserting the exemplary indwelling valve actuated urinary catheter through the urethra and locating the valve in the bladder and locating the valve actuator along the penis. To help with insertion or removal of the indwelling valve actuated urinary catheter, a special tool or a small size balloon catheter may be used. A user may then manipulate the valve actuator by moving proximal and distal nodules with respect to each other to change an offset distance therebetween and open the valve. Urine will then flow through the inlet port and into the inner conduit of the inner catheter. Urine will then flow out of the penis to expel urine from the bladder. A user may release the valve actuator and a spring element may return the proximal and distal nodules to a closed position, or position wherein the valve is closed.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figures 1, 2:
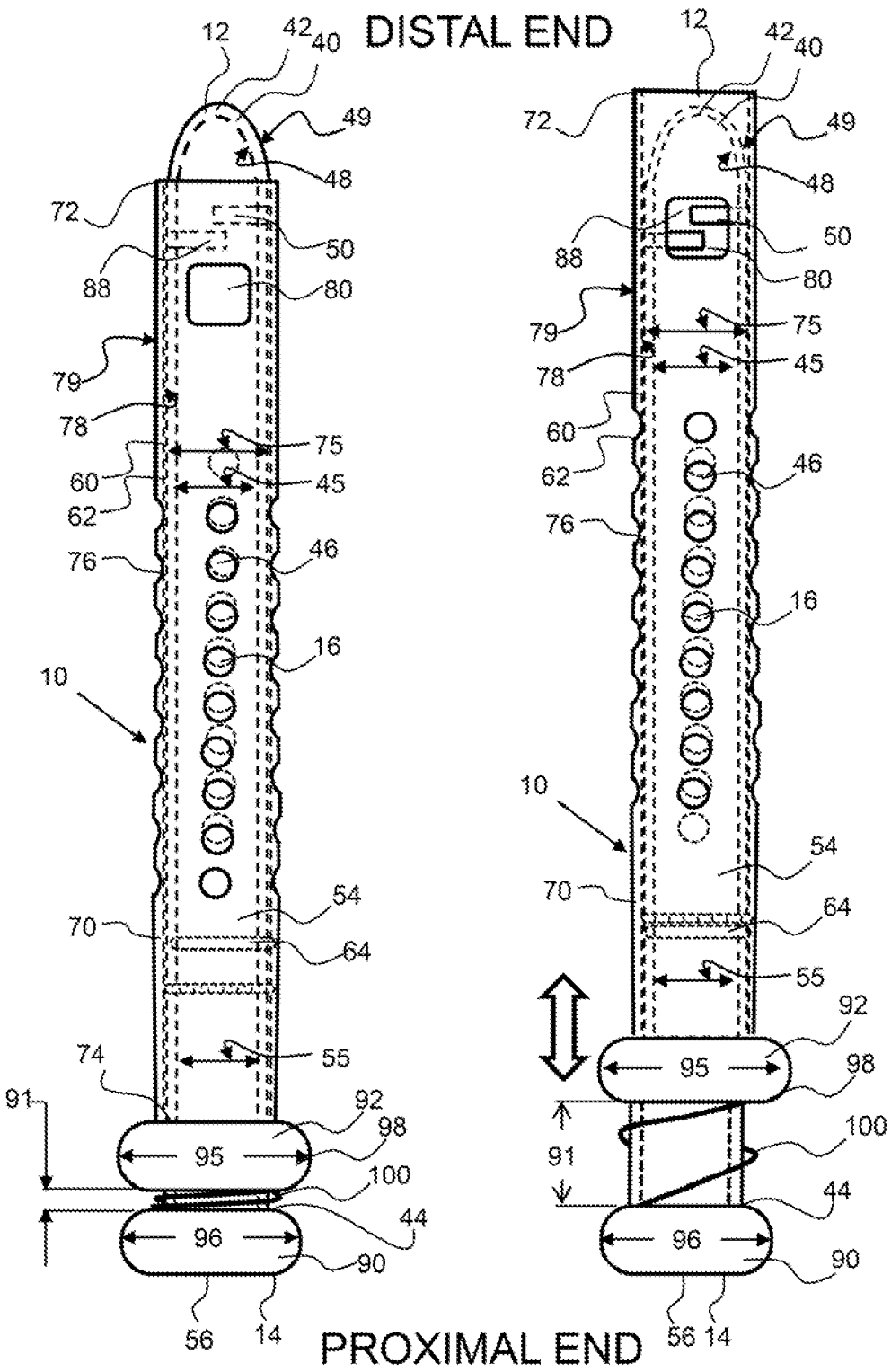
FIG. 1 shows an exemplary indwelling valve actuated urinary catheter having a valve in a closed position configured on the distal end of the catheter and a valve actuator configured on the proximal end.
FIG. 2 shows an exemplary indwelling valve actuated urinary catheter having a valve in a open position configured on the distal end of the catheter and a valve actuator configured on the proximal end.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Referring now to FIGS. 1 and 2, an exemplary indwelling valve actuated urinary catheter 10 has a valve 88 on the distal end 12 of the catheter and a valve actuator 98 configured on the proximal end 14 of the catheter. The valve comprises an inlet port 50 configured on the inner catheter 40 and a valve window 80 configured in the catheter sheath 70. As shown in FIG. 1, the valve 88 is in a closed position with the inlet ports 50 and the valve window 80 offset and not aligned. As shown in FIG. 2, the valve 88 is in an open position with the inlet ports 50 and valve window 80 aligned to allow fluid, such as urine from the bladder to flow into the inner conduit 54 of the catheter that has an inner conduit diameter 55. The inner conduit allows urine to pass from the valve 88 to the conduit outlet 56. The valve is actuated by a valve actuator 98 configured on the opposing and proximal end of the catheter. The valve actuator comprises a proximal nodule 90 and a distal nodule 92 coupled together by a spring element 100. The catheter sheath 70 is coupled with the distal nodule 92 and when the offset distance 91 between the proximal and distal nodule is expanded, as shown in FIG. 2, the catheter sheath slides up to align the valve window 80 with the inlet ports 50. The spring element 100 may retract the catheter sheath 70 to close the valve 88 after urine has been expelled through the catheter and penis. The proximal nodule 90 has a diameter 96 and the distal nodule 92 has a diameter 95, and these diameters may be different, wherein the distal nodule may be bigger in dimension or have a larger diameter than the proximal nodule. These different diameters may aid in locating and moving the distal nodule with respect to the proximal nodule.

The inner catheter 40 has a length from a distal end 42 to the proximal 44. The inner catheter 40 is coupled with the proximal nodule 90, but not with the distal nodule 92. The inner catheter has an inner catheter diameter 45 an inside surface 48 and an outside surface 49. The catheter sheath 70 has a length from a distal end 72 to the proximal 74. The catheter sheath 70 is coupled with the distal nodule 92, but not with the proximal nodule 90. The catheter sheath has an inner catheter diameter 75 an inside surface 78 and an outside surface 79. The catheter sheath extends around the inner catheter and slides along the length axis when the valve actuator is manipulated. A lubricant 62, such as a hydrogel may be configured in the interface 60 between the inner catheter and the catheter sheath.

A plurality of prostate apertures 16 are configured in an exemplary indwelling valve actuated urinary catheter 10 to allow prostate secretions to pass into the inner conduit 54 of the catheter. The catheter sheath 70 has prostate apertures 76 and the inner catheter 40 has prostate apertures 46, and these apertures may be at least partially aligned when the valve is in a closed and/or open position.

A retainer feature 64 may keep the valve in an open position after it is manually opened and may comprise an enlarged outside surface feature of the inner catheter and a retainer ring on the inside surface of the catheter sheath 70. An interference between these two features in the interface 60 may require a force to push the retainer ring over the enlarged outside surface feature. After the retainer ring as passed over the enlarged outside surface feature of the inner catheter, the valve may stay open. The spring element may be selected to have a retraction force that is not sufficient to pull the retainer ring over the enlarged outside surface feature of the inner catheter. A person may have to manually move the distal nodule 92 to move the retainer ring over the enlarged outside surface feature, to close the valve.

Figure 3:
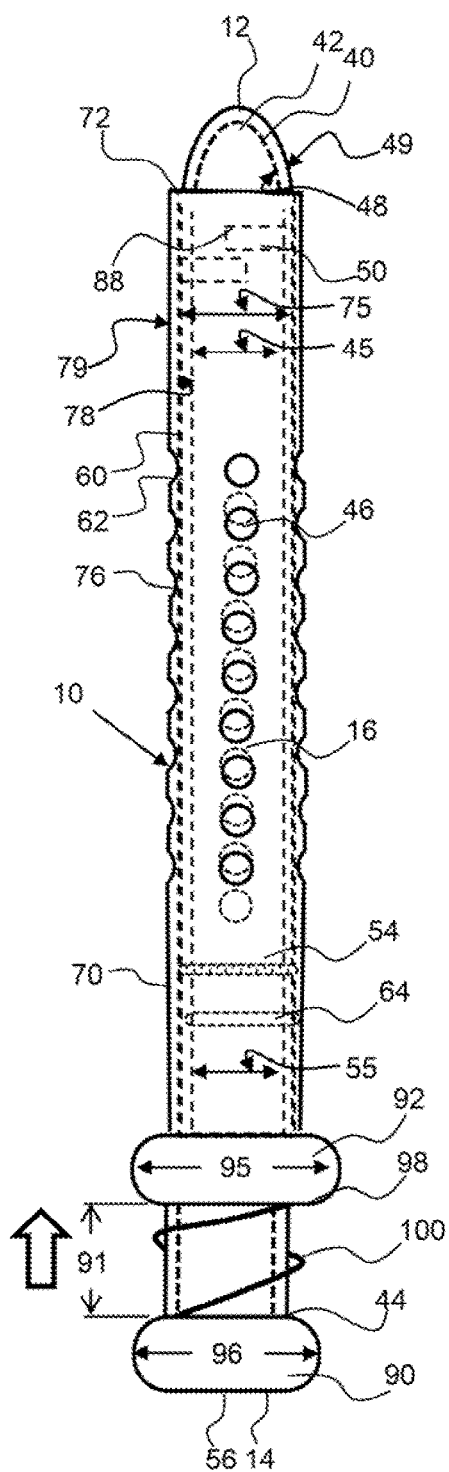
FIG. 3 shows an exemplary indwelling valve actuated urinary catheter having a valve in a closed position configured on the distal end of the catheter and a valve actuator configured on the proximal end.
Figure 4:
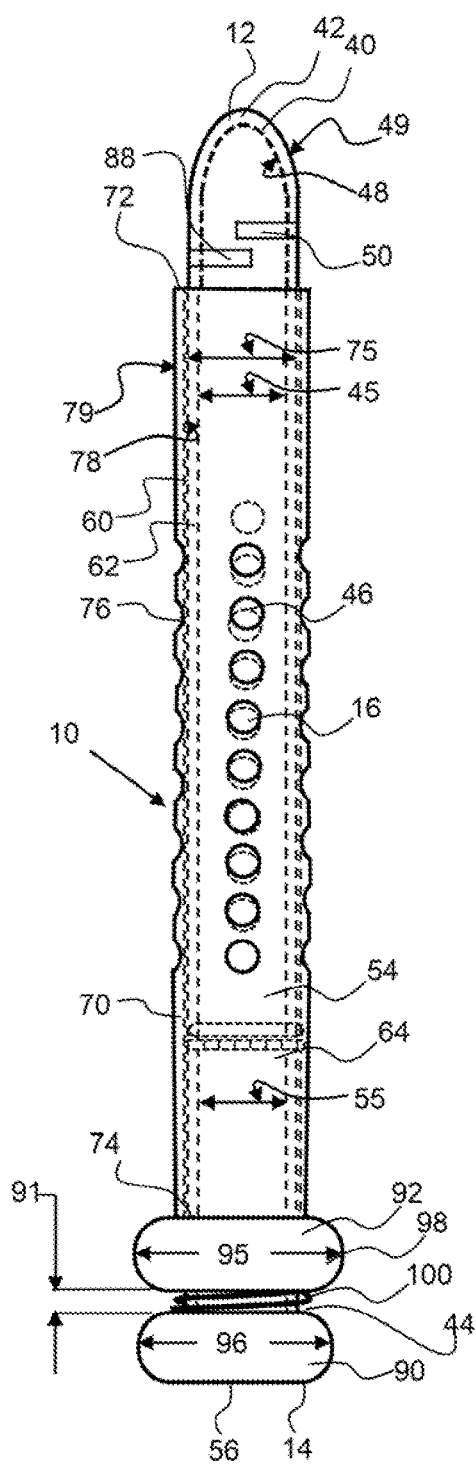
FIG. 4 shows an exemplary indwelling valve actuated urinary catheter having a valve in an open position configured on the distal end of the catheter and a valve actuator configured on the proximal end.

Referring to FIGS. 3 and 4, the exemplary indwelling valve actuated urinary catheter 10 has many of the features as shown in FIGS. 1 and 2, but has a different type of valve. In this embodiment, the valve 88 is in a closed position when the distal nodule 92 is spaced apart from the proximal nodule 90. The catheter sheath extends over the inlet ports 50 and therefore seals the valve closed, as shown in FIG. 3. As shown in FIG. 4, the distal nodule 92 is moved toward the proximal nodule 90 and the valve 88 is in an open position, with the inlet ports now exposed. A user would manually manipulate the valve actuator 98 to bring together the proximal nodule 90 and distal nodule 92 to open the valve 88. In this embodiment, the force of spring element 100 keeps the proximal and distal nodules forced apart to keep the valve closed. The valve would stay open when the retainer feature 64 is engaged, as described herein, and would require some additional force to move the catheter sheath over the retainer feature to open the valve.

Figure 5:
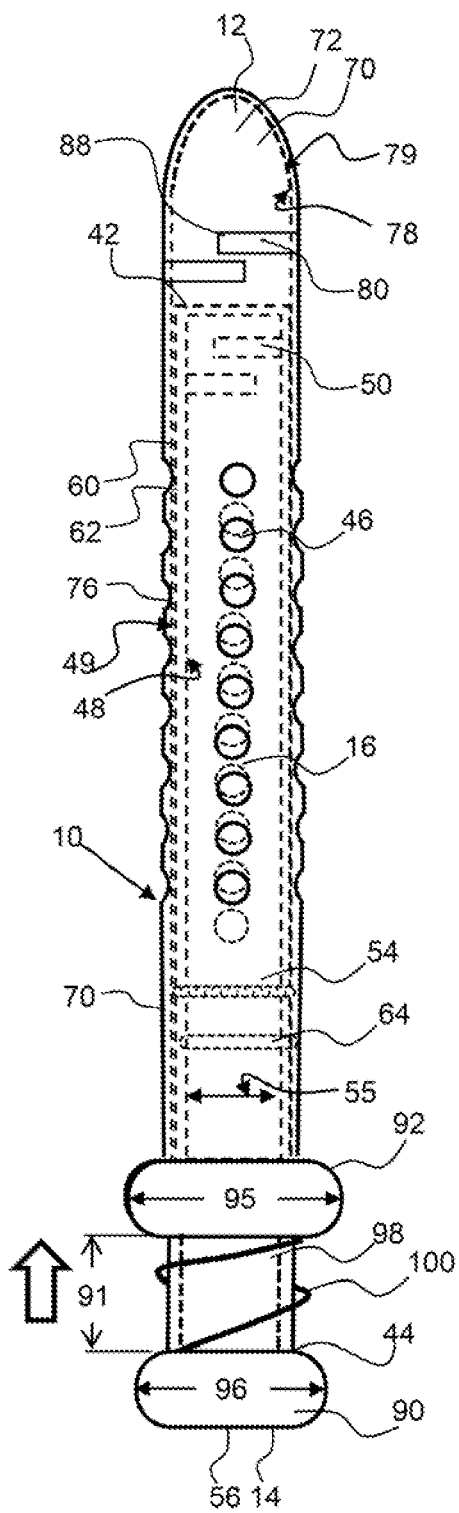
FIG. 5 shows an exemplary indwelling valve actuated urinary catheter having a valve in a closed position configured on the distal end of the catheter and a valve actuator configured on the proximal end.
Figure 6:
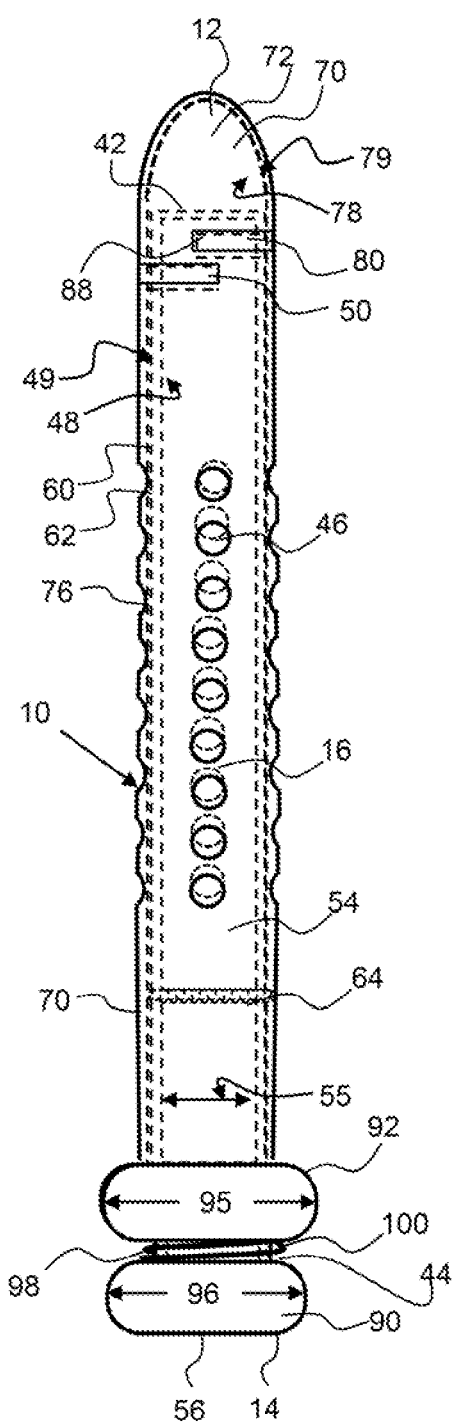
FIG. 6 shows an exemplary indwelling valve actuated urinary catheter having a valve in an open position configured on the distal end of the catheter and a valve actuator configured on the proximal end.

Referring to FIGS. 5 and 6, the exemplary indwelling valve actuated urinary catheter 10 has many of the features as shown in FIGS. 1 to 4, however the inner catheter 40 is moved with respect to sheath 70 to align an inlet port 50 in the inner catheter with a window 80 on the sheath. As shown in FIG. 5, the valve 88 is in a closed position and the spring element 100 is exerting an extension force to keep the distal end 42 and inlet port 50 of the inner catheter in a position more proximal to the valve actuator 98 than when in an open position, as shown in FIG. 6. The inlet port and window are not aligned in FIG. 5, however when a user manually manipulates the proximal nodule 90, by moving it closer to the distal nodule 92 and reducing the offset distance, the inlet port 50 becomes aligned with the window 80 to allow urine to pass into the inner conduit 54 of the inner catheter 40. In this embodiment, the force of spring element 100 keep the proximal and distal nodules forced apart and keeps the valve closed. When a user moves the inner catheter within the catheter sheath, the retainer feature may be engaged, wherein a detent and/or protrusion at the interface 60 move over each other to secure the valve 88 in an open position.

Figure 7:
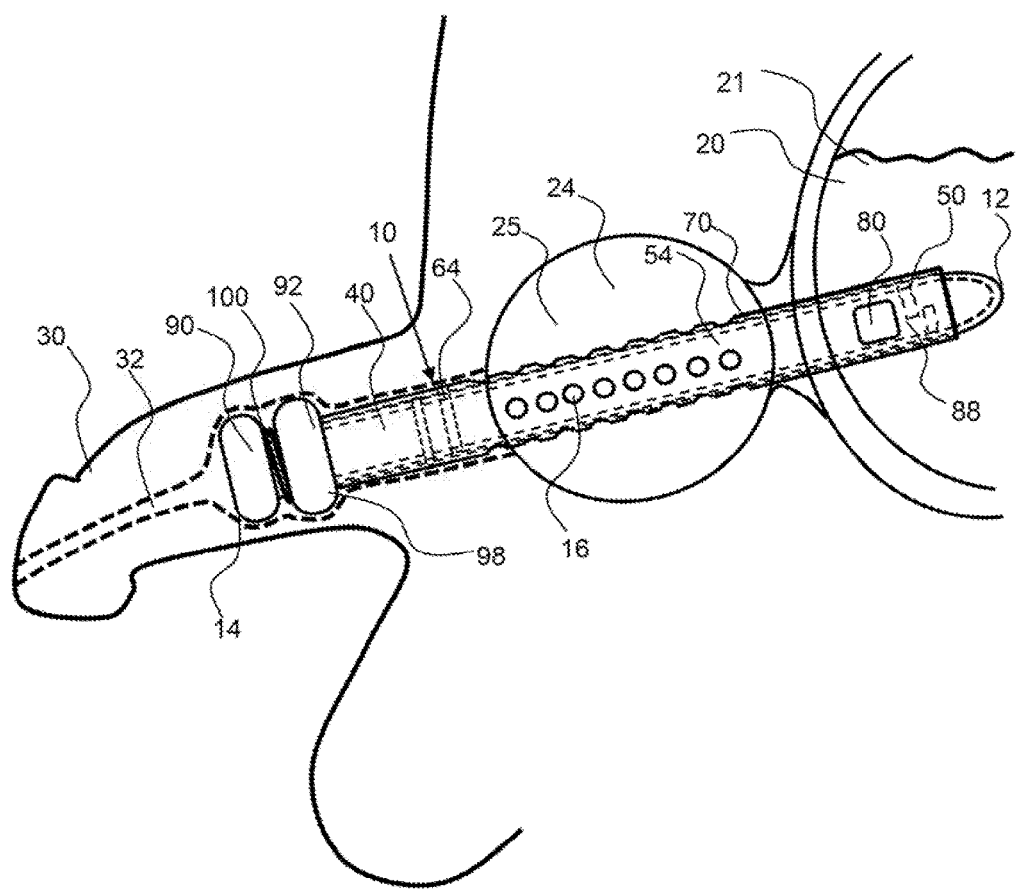
FIG. 7 shows an exemplary indwelling valve actuated urinary catheter inserted into a urethra with the distal end and valve configured within the bladder and the valve actuator configured within the penis.
Figure 8:
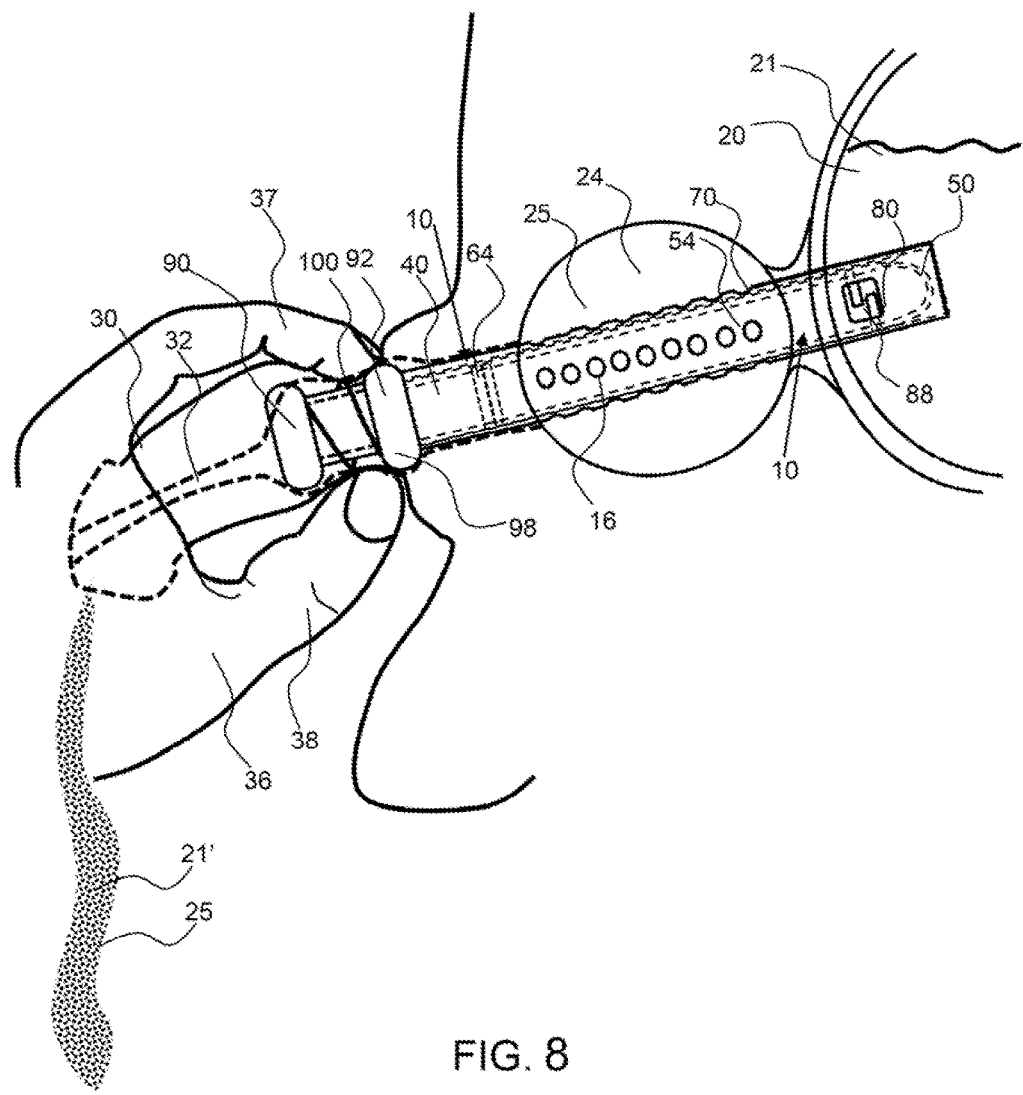
FIG. 8 shows an exemplary indwelling valve actuated urinary catheter inserted into a urethra with the distal end and valve configured within the bladder and the valve actuator configured within the penis and the valve being opened by a person's hand.

As shown in FIG. 7, an exemplary indwelling valve actuated urinary catheter 10 is inserted into a urethra 32 with the distal end 12 and valve 88 configured within the bladder 20 and the valve actuator configured within the penis 30. The valve is in a closed position and urine 21 within the bladder is not leaking into the inner conduit of the catheter. The catheter remains void of urine until the catheter valve is opened. The indwelling valve actuated urinary catheter 10 extends through the prostate 24 and the prostate apertures 16 allow prostate secretions 25 to flow into the inner catheter 40.

As shown in 8, an exemplary indwelling valve actuated urinary catheter is inserted into a urethra 32 with the distal end 12 and valve 88 configured within the bladder 20 and the valve actuator 98 configured within the penis 30. The valve 88 is being manually opened by the person's hand 36. The person is using their finger 37 and thumb 38 to separate the proximal 90 and distal nodule 92 to open the valve 88. The person is opening the valve in situ. Urine 21' and prostate secretions 25 are being expelled from the penis.

Figure 9:
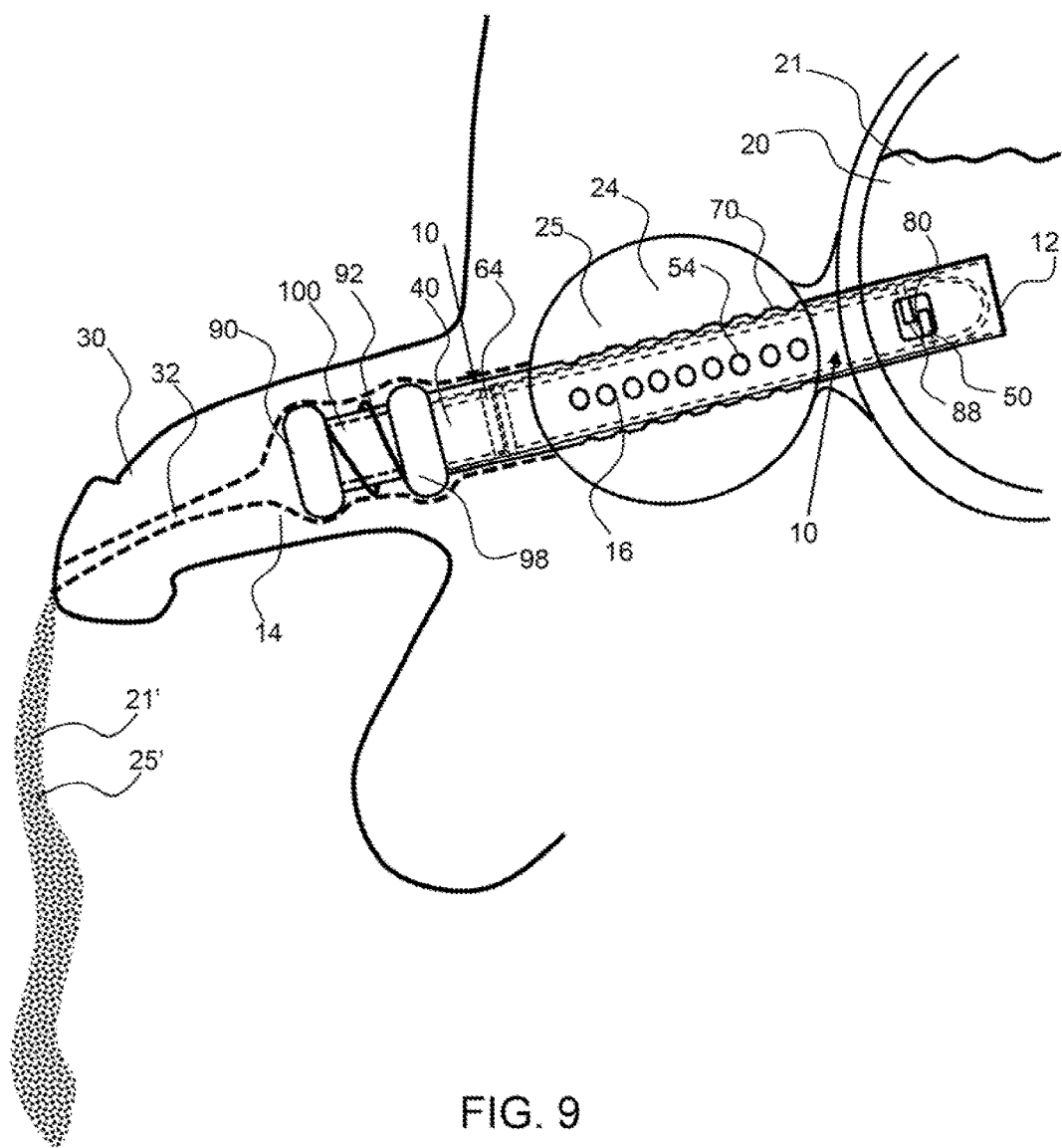
FIG. 9 shows an exemplary indwelling valve actuated urinary catheter inserted into a urethra with the distal end and valve configured within the bladder and the valve remaining in an open position by the retainer feature.

As shown in FIG. 9, the retaining feature 64 is engaged and the valve remains open without holding the nodules in a separated configuration. This enables a person to continue to expel urine 21' and prostate secretions 25 without squeezing their penis after actuating the valve actuator.

Figure 10:
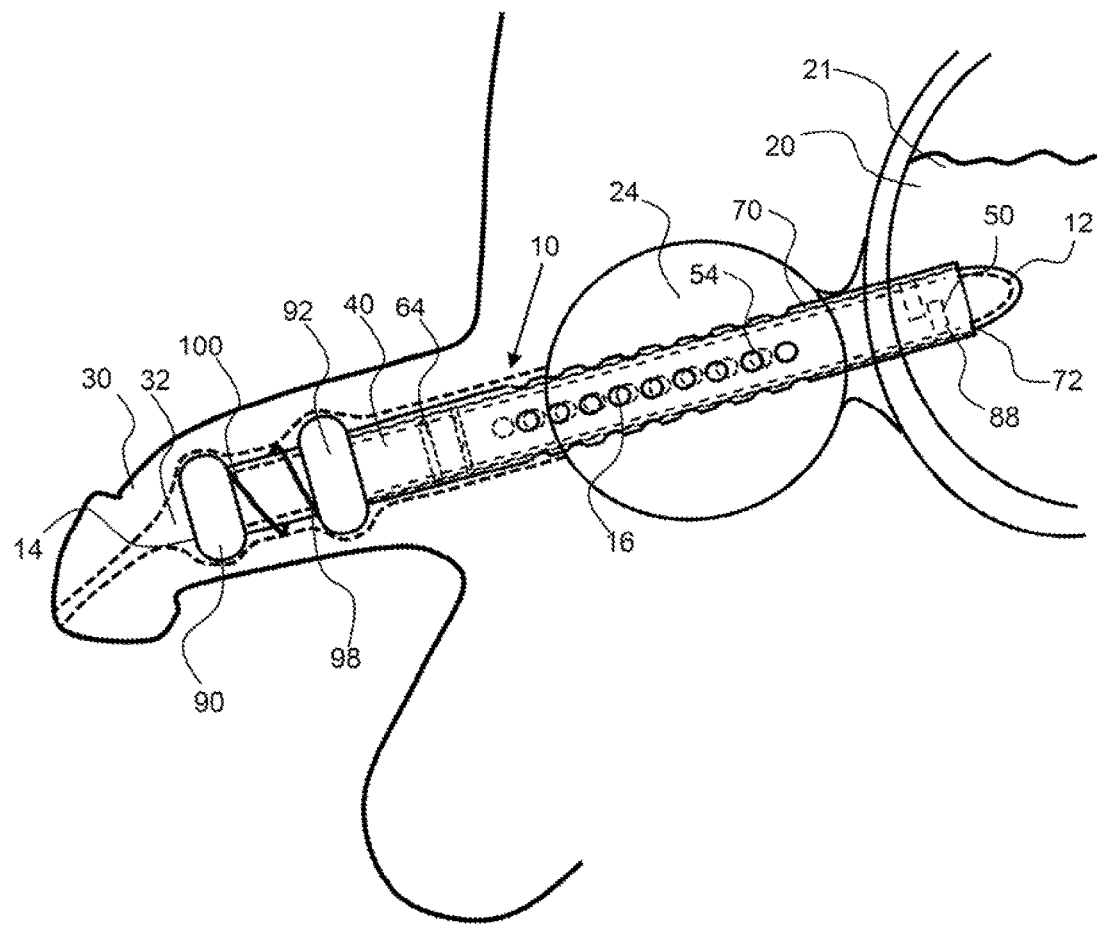
FIG. 10 shows an exemplary indwelling valve actuated urinary catheter inserted into a urethra with the distal end and valve configured within the bladder and the valve actuator configured within the penis.

As shown in FIG. 10, an exemplary indwelling valve actuated urinary catheter 10 is inserted into a urethra 32 with the distal end 12 and valve 88 configured within the bladder 20 and the valve actuator configured within the penis 30. The valve is in a closed position and urine 21 within the bladder is not leaking into the inner conduit of the catheter. The catheter remains void of urine until the catheter valve is opened. The second nodule 92 is forced toward the distal end 12 by the spring element 100 and this keeps the distal end 72 of the sheath 40 configured over the inlet port 50, thereby sealing the valve 88 closed.

Figure 11:
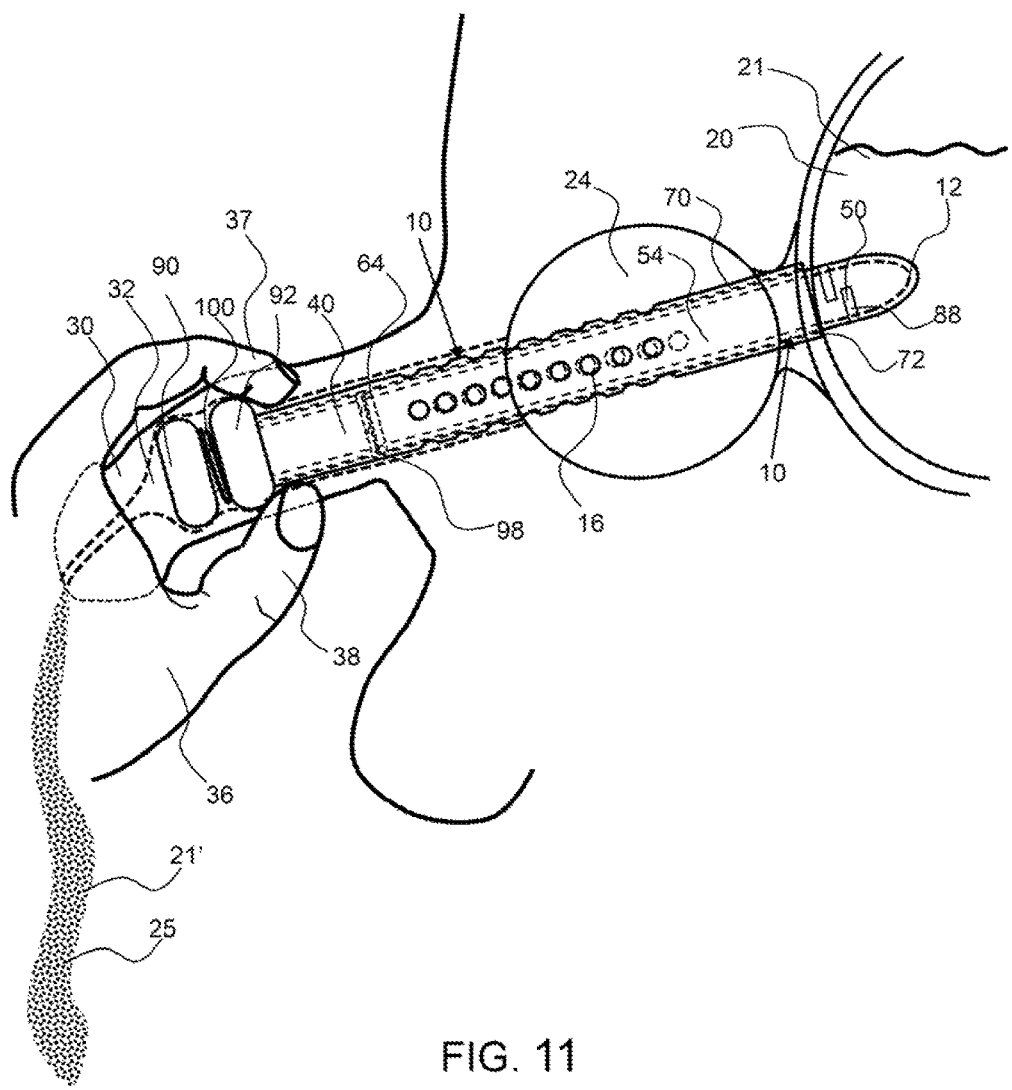
FIG. 11 shows an exemplary indwelling valve actuated urinary catheter inserted into a urethra with the distal end and valve configured within the bladder and the valve actuator configured within the penis and the valve being opened by a person's hand.

As shown in FIG. 11, an exemplary indwelling valve actuated urinary catheter 10 is inserted into a urethra 32 with the distal end 12 and valve 88 configured within the bladder 20 and the valve actuator 98 configured within the penis 30. The valve 88 is being manually opened by the person. The distal nodule 92 is being brought closer to the proximal nodule 90 by the person's finger 37 and thumb 38. Moving the distal nodule toward the proximal nodule moves the sheath 70 over the inner catheter 40 to expose the inlet port 50 and allow urine 21 to pass from the bladder 20 into the inner conduit 54. The person is opening the valve in situ. Urine 21' and prostate secretions 25 are being expelled from the penis.

Figure 12:
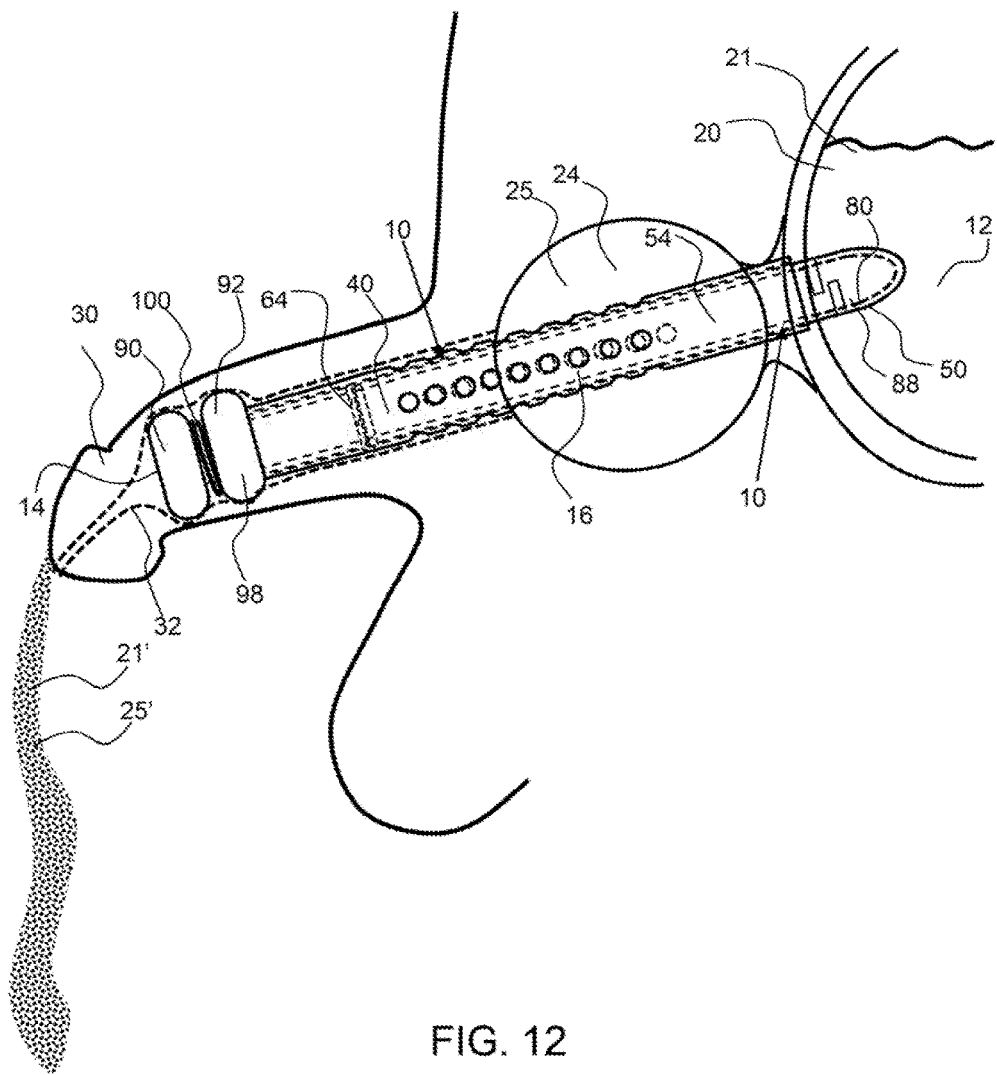
FIG. 12 shows an exemplary indwelling valve actuated urinary catheter inserted into a urethra with the distal end and valve configured within the bladder and the valve remaining in an open position by the retainer feature.

As shown in FIG. 12, the retaining feature 64 is engaged and the valve 88 remains open without holding the distal nodule in place manually. This enables a person to continue to expel urine 21' and prostate secretions 25' without squeezing their penis after actuating the valve actuator 98.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An indwelling valve actuated urinary catheter comprising:
    a) a length from a proximal end to a distal end of the indwelling valve actuated urinary catheter;
    b) an inner catheter comprising:
        i) a distal end;
        ii) a proximal end; and
        iii) a length from said distal end to said proximal end of the inner catheter;
        iv) an inner conduit;
    c) a catheter sheath having a length from a distal end to a proximal end of said catheter sheath;
        wherein the catheter sheath extends around the inner catheter;
    d) a valve configured on a distal end of said indwelling valve actuated urinary catheter; the value comprising:
        i) an inlet port through the inner catheter for a flow of urine to pass into an inner conduit of the inner catheter;
        wherein the catheter sheath extends over the inlet port while the indwelling valve actuated urinary catheter is in a closed position;
        wherein the inlet port is configured in a bladder during use of the indwelling valve actuated urinary catheter to drain urine from said bladder;
    e) a valve actuator configured on a proximal end of said indwelling valve actuated urinary catheter, said valve actuator comprising:
        i) a proximal nodule attached to the inner catheter;
        ii) a distal nodule attached to the catheter sheath;
        wherein an offset distance between the proximal and distal nodules is changed manually by moving the distal nodule with respect to the proximal nodule which moves the catheter sheath to expose the inlet port to allow urine to pass into the inner conduit of the inner catheter, through the inner conduit and out of a penis; and
    wherein the valve actuator is configured in the penis during use of the indwelling valve actuated urinary catheter to drain urine from said bladder;
    wherein the distal end of the catheter sheath is more distal to the inlet port while in a closed position;
    wherein the catheter sheath extends over the inlet port to seal the valve while in a closed position; and
    wherein the catheter sheath is moved by decreasing the offset distance between the proximal and distal nodules to move the distal end of the catheter sheath to a position more proximal to the proximal end of the indwelling valve actuated urinary catheter to expose the inlet port and open the valve to allow urine to pass into the inner conduit of the inner catheter and be expelled through the penis.

2. The indwelling valve actuated urinary catheter of claim 1, wherein the valve actuator comprises a spring element that provides an extension force to increase the offset distance between the proximal and distal nodules.

3. The indwelling valve actuated urinary catheter of claim 1, wherein the valve actuator comprises a spring element comprising a spring that coils around the inner catheter.

4. The indwelling valve actuated urinary catheter of claim 1, wherein the proximal and distal nodules are toroid shaped and have an outer diameter that is greater than an outer diameter of the catheter sheath.

5. The indwelling valve actuated urinary catheter of claim 4, wherein the distal nodule has a diameter and the proximal nodule has a diameter that is different than the distal nodule diameter.

6. The indwelling valve actuated urinary catheter of claim 1, wherein the inner catheter comprises an inner prostate aperture that extends through the inner catheter to allow passage of prostate secretions into the inner conduit; and wherein the sheath comprises a sheath prostate aperture that is aligned with the inner prostate aperture for passage of prostate secretions into the inner conduit.

7. The indwelling valve actuated urinary catheter of claim 1, further comprising a retaining feature that retains the catheter sheath in an offset position while the distal nodule is moved with respect to the proximal nodule to change the offset distance.

8. An indwelling valve actuated urinary catheter comprising:
    a) a length from a proximal end to a distal end;
    b) an inner catheter comprising:
        i) a distal end;
        ii) a proximal end; and iii) a length from said distal end to said proximal end of the inner catheter;
iv) an inner conduit;
c) a catheter sheath having a length from a distal end to a proximal end of said catheter sheath;
wherein the catheter sheath extends around the inner catheter and comprises
i) a window;
d) a valve configured on a distal end of said indwelling valve actuated urinary catheter; the value comprising:
i) an inlet port through the inner catheter for a flow of urine to pass into an inner conduit of the inner catheter;
wherein the catheter sheath extends over the inlet port while the indwelling valve actuated urinary catheter is in a closed position;
wherein the inlet port is configured in a bladder during use of the indwelling valve actuated urinary catheter to drain urine from said bladder;
e) a valve actuator configured on a proximal end of said indwelling valve actuated urinary catheter, said valve actuator comprising:
i) a proximal nodule attached to the inner catheter;
ii) a distal nodule attached to the catheter sheath;
wherein an offset distance between the proximal and distal nodules is changed manually by moving the distal nodule with respect to the proximal nodule which moves the catheter sheath to align the window with the inlet port to allow urine to pass into the inner conduit of the inner catheter, through the inner conduit and out of a penis;
wherein the valve actuator is configured in the penis during use of the indwelling valve actuated urinary catheter to drain urine from said bladder.

9. The indwelling valve actuated urinary catheter of claim 8, further comprising a spring element between the proximal nodule and distal nodule.

10. The indwelling valve actuated urinary catheter of claim 9, wherein the spring element provides a retraction force to reduce the offset distance between the proximal and distal nodules.

11. The indwelling valve actuated urinary catheter of claim 9, wherein the spring element provides an extension force to increase the offset distance between the proximal and distal nodules.

12. The indwelling valve actuated urinary catheter of claim 8, further comprising a retaining feature that retains the catheter sheath in an offset position while the distal nodule is moved with respect to the proximal nodule.

13. A method of urinating comprising the steps of:
a) providing an indwelling valve actuated urinary catheter comprising:
i) a length from a proximal end to a distal end;
ii) an inner catheter comprising:
a distal end;
a proximal end; and
a length from said distal end to said proximal end of the inner catheter portion;
an inner conduit;
iii) a catheter sheath having a length from a distal end to a proximal end of said catheter sheath;
wherein the catheter sheath extends around the inner catheter;
iv) a valve configured on a distal end of said indwelling valve actuated catheter; the value comprising:
an inlet port through the inner catheter for a flow of urine to pass into an inner conduit of the inner catheter;
wherein the catheter sheath extends over the inlet port while the indwelling valve actuated urinary catheter is in a closed position;
wherein the inlet port is configured in a bladder during use of the indwelling valve actuated urinary catheter to drain urine from said bladder;
v) a valve actuator configured on a proximal end of said indwelling valve actuated catheter, said valve actuator comprising:
a proximal nodule attached to the inner catheter;
a distal nodule attached to the catheter sheath;
wherein an offset distance between the proximal and distal nodules is manually changed to move the catheter sheath with resect to the inner catheter to expose the inlet port and allow urine to pass into said inner conduit of the inner catheter;
wherein the sheath comprises a window; and
wherein the valve actuator is configured in a penis during use of the indwelling valve actuated urinary catheter to drain urine from said bladder;
b) inserting the indwelling valve actuated urinary catheter into a urethra of said penis to position the valve in a bladder and the valve actuator in the penis;
c) manually changing an offset distance between the proximal and distal nodules to move the catheter sheath along the length of the inner catheter to expose the inlet port and open the valve;
wherein the step of manually changing an offset distance between the proximal and distal nodules aligns the window with the inlet port to allow urine to pass into the inner conduit of the inner catheter, through the inner conduit and out of the penis; and
d) passing urine from the bladder through the inlet port, through the inner conduit and out of the penis.

14. The method of urinating of claim 13, further comprising a spring element, wherein the spring element is a spring that coils around the inner catheter.

15. The method of urinating of claim 13, wherein the inner catheter comprises an inner prostate aperture that extends through the inner catheter to allow passage of prostate secretions into the inner conduit; wherein the sheath comprises a sheath prostate aperture that is aligned with the inner prostate aperture for the passage of prostate secretions into the inner conduit, and wherein the step of manually changing an offset distance between the proximal and distal nodules to open the valve, allows said prostate secretions to flow from the inner conduit and be expelled through the penis.

16. The method of urinating of claim 13, wherein the indwelling valve actuated urinary catheter further comprises a retaining feature that retains the catheter sheath in an offset position while the distal nodule is moved with respect to the proximal nodule to change the offset distance.

* * * * *